United States Patent [19]

Thimineur et al.

[11] Patent Number: 4,784,844

[45] Date of Patent: Nov. 15, 1988

[54] VOLATILE SILICONE-WATER EMULSIONS AND METHODS OF PREPARATION AND USE

[75] Inventors: Raymond J. Thimineur, Scotia; Frank J. Traver, Troy, both of N.Y.

[73] Assignee: General Electric Company, Waterford, N.Y.

[21] Appl. No.: 24,873

[22] Filed: Mar. 17, 1987

Related U.S. Application Data

[63] Continuation of Ser. No. 449,081, Dec. 13, 1982, abandoned, which is a continuation of Ser. No. 099,956, Dec. 3, 1979, abandoned.

[51] Int. Cl.$^4$ .................... A61K 7/06; A61K 7/38; A61K 7/42; A61K 9/10
[52] U.S. Cl. ........................... 424/65; 424/59; 424/68; 424/70; 514/694; 514/846; 514/847; 514/937; 514/944; 514/969
[58] Field of Search ............... 424/65, 68; 514/941

[56] References Cited

U.S. PATENT DOCUMENTS

| | | | |
|---|---|---|---|
| Re. 29,814 | 10/1978 | Snyder | 424/184 |
| 2,990,377 | 6/1961 | May | 252/312 |
| 3,428,560 | 2/1969 | Olsen | 252/817 |
| 3,541,205 | 11/1970 | Hardigan et al. | 424/184 X |
| 3,624,120 | 11/1971 | Yetter | 424/184 X |
| 3,641,239 | 2/1972 | Mohrlok | 424/184 X |
| 3,836,647 | 9/1974 | Lange | 424/184 |
| 3,953,591 | 4/1976 | Snyder | 424/184 |
| 4,010,110 | 3/1977 | Consentino et al. | 514/941 |
| 4,052,331 | 10/1977 | Damoulin | 252/312 |
| 4,194,988 | 3/1980 | Schneider et al. | 252/312 |

FOREIGN PATENT DOCUMENTS

| | | | |
|---|---|---|---|
| 2033191 | 4/1970 | France | 424/184 |
| 48-19941 | 6/1973 | Japan | 424/184 |
| 804369 | 11/1958 | United Kingdom | 424/184 |
| 892819 | 3/1962 | United Kingdom | 424/184 |
| 926914 | 5/1963 | United Kingdom | 424/184 |
| 1206790 | 9/1970 | United Kingdom | 424/184 |

OTHER PUBLICATIONS

Plein et al., 2/1963, Journ. of Pharm. Assoc., pp. 79 to 85.

Taikowski et al., 12/1953, Proceedings of the Scientific Section, Toilet Goods Assoc., pp. 1 to 7.

Levin, Manufacturing Chemist, 4/1955, vol. 26, No. 4, pp. 157-160.

Todd et al., American Perfumer & Cosmetics, 1970, vol. 86, pp. 112 to 115.

Holbrook et al., J.A.C.S., 2/1960, vol. 82, No. 4, pp. 825-837.

G. E. Silicones Cosmetics & Toiletries Handbook, Publication CS-5A, pp. 2 to 12.

*Primary Examiner*—Dale R. Ore

[57] ABSTRACT

The present invention provides silicone-water emulsions formed from volatile cyclic polysiloxanes which are emulsified with a preblended mixture of water and a combination of emulsifying agents. Highly ethoxylated nonionic emulsifying agents are particularly well-suited for the formation of stable silicone-water emulsions from volatile cyclic polysiloxanes. These volatile silicone-water emulsions can be combined with epidermal enhancing agents for cosmetic and medicinal purposes.

21 Claims, No Drawings

VOLATILE SILICONE-WATER EMULSIONS AND METHODS OF PREPARATION AND USE

This application is a continuation of application Ser. No. 449,081 filed 12/13/82 which is a continuation of 099,956 12/3/79, both now abandoned.

BACKGROUND OF THE INVENTION

The present invention discloses compositions of matter and methods for producing stable silicone-water emulsions of volatile cyclic polysiloxanes without the need for milling or homogenization and which are particularly useful in cosmetic and medicinal applications.

The silicone-water emulsion composition of the present invention is particularly well-suited for serving as a vehicle for the application of epidermal enhancing agents. The expression "epidermal enhancing agents" refers to those compositions having properties generally considered as being beneficial when applied to portions of the body. For example, such agents include a wide range of cosmetics and medical and pharmaceutical compounds.

In the cosmetic category there are many types of products which can be beneficially applied to the skin in a silicone emulsion form. For example, such cosmetics would include cream eye shadows, foundations, blushes, lip gloss, mascara and eyeliner, cover-up-type compositions and wrinkle creams, moisturizers, acne cover-up depilatories and cuticle removers, etc.

Such emulsions can also be used for cleansing purposes and may take the form of shampoos, soaps, conditioners and moisturizers. Additionally, hair dyes may be applied in a silicone-water emulsion vehicle.

Additional cosmetic uses include the application of perfumes, colognes and sachets to the body. Among the particularly useful applications would be deodorants and antiperspirants.

Among the many medical uses of such an emulsion vehicle would be first aid uses such as burn ointments and the application of antiseptics. Furthermore, corn, wart and callous removing agents, for example, can be successfully applied to the skin in such a silicone-water emulsion vehicle.

Of course, the consistency of the silicone-water emulsion of the present invention can be varied through many degrees from a lotion-like consistency through cold cream-like pastes up to gel-type ointments or salves on the order of a petroleum jelly.

Silicones are synthetic polymers ordinarily commercially prepared from chlorosilane monomers and available in the form of fluids, resins and rubber gums. Of particular interest to the cosmetic industry are those polymers formulated into emulsions, greases, pastes, etc. In these formulations a wide variety of materials may be used in conjunction with the silicones.

Monomeric chlorosilanes are very reactive volatile materials which readily react with moisture to form silicones and byproduct hydrochloric acid. Thus, in the presence of moisture they are considered corrosive materials and may have hazardous properties and must be handled with care. However, after processing into silicone polymers these materials become bland and inert substances. Silicones may be further formulated with other materials to produce various end use compositions and often the physiological effect of the finished composition is determined by the nature of the nonsilicone component.

The toxocological properties of silicones have been widely studied and, as a group, polymeric silicone fluids and resins ordinarily have a very low order of toxicity. Considered from a practical viewpoint, the hazards they present are exceedingly minor. Silicone fluid polymers have been the subject of skin irritation and sensitization patch test studies and are typically shown to be safe. The low level of toxicity of silicone materials has even lead to the acceptance and successful use of silicone fluids in medical and dental applications.

Silicone fluids generally provide excellent protection against water-borne irritants such as harsh detergents and other household cleaning specialties. The chemical inertness and excellent water-repellency of silicone fluids are the major reasons for their effectiveness in preventing dermatitis. Silicones may also function as emollients, and provide pleasant non-stick "feel". Superior suntan lotions and creams can be prepared using silicones, since the silicone fluid is a carrier for the sunscreening agent and resists wash-off by either bathing or perspiration.

Emulsions containing volatile silicone cyclic polysiloxanes have been previously formulated by utilizing emulsifying agents such as dodecyl benzene sulfonic acid, however, these systems require milling or homogenization in order to emulsify the immiscible phases. It is possible to emulsify preparations of this type having only up to about 55% concentration of volatile cyclics and emulsions of this type are frequently utilized to carry out emulsion-type polymerization of cyclic such as octamethyltetrasiloxane.

The present invention provides a method which makes it possible to emulsify larger concentrations of cyclic polysiloxanes while at the same time eliminating the necessity of milling or homogenization. Additionally, the present invention provides stable emulsions of cyclic polysiloxanes such that these emulsions do not ordinarily "break" under normal storage and use conditions even when the concentration of volatile cyclic polysiloxane is 80% or more. This is a particularly useful property for consumer oriented products since these emulsions can therefore, ideally be utilized as vehicles for conveying epidermal enhancing agents onto the skin of a user in a beneficial manner.

Furthermore, the present invention offers a system for emulsifying volatile cyclic polysiloxanes which yield opaque to transparent materials, which can be readily formulated into many consumer products and particularly antiperspirants and deodorants, etc. Other potential uses for water based cyclic emulsions are skin care products such as hand lotions, skin fresheners, hair preparations and other grooming aids. As noted above, the method of the present invention provides a means for selectively varying the consistency of these emulsions depending upon the ultimate purposes of the product.

An additional advantage resides in the fact that these silicone-water emulsions are comprised of relatively volatile cyclic polysiloxane constituents such that an emulsion vehicle base will eventually evaporate from the skin and only the beneficial epidermal enhancing agent will be left thereon.

It is therefore an object of the present invention to provide a stable silicone-water emulsion formed from volatile cyclic polysiloxanes which is suitable for cosmetic and medicinal applications.

It is another object of the present invention to provide methods of preparing such silicone-water emulsions and methods for applying epidermal enhancing agents.

SUMMARY OF THE INVENTION

The present invention provides a silicone-water emulsion and methods of preparation and uses wherein said emulsion comprises:

(A) 100 parts by weight of a cylic polysiloxane or a combination of cyclic polysiloxanes selected from theose having the general formula,

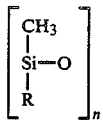

wherein n is an integer from 3 to 10, R is selected from the group consisting of —CH$_3$, —(CH$_2$)$_z$CH$_3$, —CH$_2$CH$_2$CF$_3$, —CH$_2$=CH$_2$, and —C$_6$H$_5$ and combinations thereof and z is an integer from 1 to 10;

(B) from 0.7 to 666 parts by weight of an emulsifier; and (C) from 5.0 to 960 parts by weight of water; and stirring with moderate heat until an emulsion having desired consistency is produced.

DESCRIPTION OF THE INVENTION

The present invention provides a silicone-water emulsion, which is comprised of 100 parts by weight of a cyclic polysiloxane or a combination of cyclic polysiloxanes having a general formula,

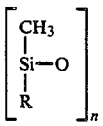

wherein n is an integer from 3 to 10, R is —CH$_3$, —(CH$_2$)$_2$CH$_3$, —CH$_2$CH$_2$CF$_3$, —CH$_2$=CH$_2$, or —C$_6$H$_5$ or combinations thereof and z is an integer from 1 to 10. The polysiloxanes designated by this formula are known as volatile silicone cyclics and this property of volatility imparts advantageous properties to the emulsion composition. Particularly useful volatile silicone cyclics are octamethyltetrasiloxane and decamethylpentasiloxane.

The volatile cyclic polysiloxane is combined with an emulsifying agent and water to form a silicone-water emulsion. The order of mixing the ingredients is not critical, however, particularly satisfactory results can be obtained when the emulsifying agents and the water are mixed together in preblend to which the volatile cyclics are added.

Preferably, the cyclic polysiloxane is added to a preblend consisting of approximately, 50 to 200 parts by weight of water, which is mixed with 100 parts by weight of one or more emulsifying agents and heated until a uniform blend is achieved.

This preblend is suitable for producing a paste-like silicone-water emulsion, however, if a more liquidous or lotion-like consistency is desired, there may range up to 2,000 or more parts water per 100 parts of the emulsifying agents. The emulsifying agents may be nonionic, anionic, cationic or amphoteric but of particular importance are those classes of nonionic emulsifiers which are highly ethoxylated. The ethoxylated fatty acids, ethoxylated and non-ethoxylated sorbitan esters, ethoxylated alkyl phenols, and ethoxylated ethers provide the best results.

Examples of emulsifiers which may be used to formulate the silicone-water emulsions of the present invention are included in but not limited by the following list:

(1) ethoxylated fatty acids like:
polyoxyethylene 8 stearate
polyoxyethylene 40 stearate
polyoxyethylene 50 stearate (2) sorbitan esters like:
sorbitan monolaurate
sorbitan monopalmitate
sorbitan monostearate
sorbitan tristearate
sorbitan monooleate
sorbitan trioleate (3) ethoxylated sorbitan esters
polyoxyethylene (20) sorbitan monolaurate
polyoxyethylene (4) sorbitan monolaurate
polyoxyethylene (20) sorbitan monopalmitate
polyoxyethylene (20) sorbitan monostearate
polyoxyethylene 20 sorbitan tristearate
polyoxyethylene 20 sorbitan monooleate
polyoxyethylene 5 sorbitan monooleate
polyoxyethylene 20 sorbitan trioleate (4) ethoxylated ethers like:
polyoxyethylene 4 lauryl ether
polyoxyethylene 23 lauryl ether
polyoxyethylene 20 cetyl ether
polyoxyethylene 10 stearyl ether
polyoxyethylene 20 oleyl ether (5) ethoxylated alkyl phenols like
(alkyl phenoxy polyoxyethylene glycol)
(C$_8$H$_{17}$C$_6$H$_4$)(OCH$_2$CH$_2$)$_n$OH
CAS #9036-19-5
(C$_9$H$_{19}$C$_6$H$_4$)(OCH$_2$CH$_2$)$_n$OH
CAS #26-27-38-3

Approximately, 15 to 50 parts by weight of this emulsifier-water preblend is added per 100 parts by weight of the cyclic polysiloxane when a paste-like silicone-water emulsion is desired.

Up to approximately, 1000 parts of this preblend can be added per 100 parts of the volatile cyclic polysiloxane inorder to provide a low viscosity, lotion-like product.

By adjusting the various process parameters such as content of the volatile cyclic polysiloxane, emulsifying agent, and water as well as the degree of mixing, it is possible to influence the consistency of the product. The silicone-water emulsion can be made in the form of a lotion as well as a paste or cream-like consistency and can be made further viscous in the form of an ointment, salve or a gel. Each of these consistencies is, of course, chosen with regard to the desired end use of the product.

The silicone-water emulsions useful as a vehicle for applying from 0.1 to 20,000 parts by weight of one or more epidermal enhancing agents per 100 parts of the emulsion.

This broad range is intended to encompass those products consisting of nearly pure silicone-water emulsion having a small amount of epidermal enhancing agent contained therein, as well as other products which have but a small amount of silicone-water emulsion contained therein. Epidermal enhancing agent refers to an additive of a cosmetic or medicinal nature which is generally regarded as providing beneficial results when applied externally to the skin of a user. The silicone-water emulsion of the present invention is particulaly well-suited to serve as a vehicle for applying deodorant or antiperspirant agents to the body.

The preblended water-emulsifier mixture is provided by stirring with moderate heat until a uniform blend is obtained whereupon the cyclic polysiloxane is added and mixed slowly without the need for milling or homogenization. Of course, milling and homogenization may be utilized if desired and it is intended that the term "mixing" encompasses these methods as well as mere agitation. Thus, the expression "mixing" is meant to encompass a continuous process utilizing, for example, a Wener-Pfleiderer wherein individual streams of the components can be metered into a twin screw processor. Likewise, a Henschel high speed mixer, a sonolator homogenizer with a vibrating reed and a plain vessel equipped with a mechanical agitator turbine blade will all produce satisfactory results. The silicone-water-emulsifier mixture is then vigorously stirred at 20° to 80° C. until an emulsion having a desired consistency is achieved. An anti-bacterial agent such as Formalin may be added if desired.

To a 2 liter stainless steel beaker equipped with a hot plate, mechanical air stirrer and thermometer, the water and emulsifier are preblended by adding together and heating to approximately 20° to 80° C. and preferably 65° to 75° C. and stirred to achieve a uniform mixture when all the solids have melted. Then the volatile cyclic polysiloxanes, which may be octamethyltetrasiloxane or decamethylpentasiloxane or a combination of these or others are slowly added to the aqueous preblend and stirred vigorously at, approximately, 30° to 80° C. and preferably, 50° to 60° C. until a uniform, grease-like emulsion is formed. Small amount of formalin may be added once the product is uniform in order to prevent bacterial activity. Unlike many conventional silicone emulsions, neither colloid milling nor homogenization is required in order to prepare these emulsions, but these means may be utilized if desired.

The consistency of the emulsion can be controlled by the amount of water added. At a 15 to 20% water level, the emulsion has a grease-like consistency, but additional water will ower the viscosity of the system to a lotion-like consistency and even more water can be utilized in order to prepare a low viscosity emulsion. The silicone-water emulsions of the present invention are fully dispersible in water.

Additionally, the consistency of the formulation can be further modified by the quantity of the cyclic polysiloxanes added. In other words, the more cyclics—the thicker the emulsion and more grease-like it will be. A lower ratio of cyclic polysiloxanes will provide a thinner emulsion.

The emulsifiers themselves influence the consistency of the product. A solid emulsifier like polyoxyethylene 40 stearate will make the emulsion thicker and more grease-like while a more liquidous emulsifier will provide a lotion-like product.

As can be seen, a wide range of emulsion formulations can be achieved by varying any one of these process parameters: concentration of water, cyclic polysiloxane, or emulsifiers, and the type of emulsifiers, whether solid or liquid.

EXAMPLE 1

To a 2 liter stainless steel beaker was added 200 grams water, 82 grams polyoxyethylene 40 stearate, and 67 grams sorbitan monostearate which are heated at 65° to 75° C. with stirring until a uniform mixture was achieved when all the solids had melted. Whereupon, 900 grams decamethylpentasiloxane was slowly added to the aqueous system and stirred vigorously at, approximately, 50° to 60° C. in order to form a uniform grease-like emulsion. Two grams of Formalin was added once the product had achieved uniformity, in order to prevent bacterial activity. The emulsion was formed without colloid milling nor homogenization and a stable, stiff, paste-like emulsion was formed which was suitable for serving as a vehicle for applying an epidermal enhancing agent such as a deodorant or antiperspirant for application directly to the skin.

EXAMPLE 2

The procedure of Example 1 was followed but was modified by the further addition of 11% by weight of polyoxyethylene 20 sorbitan monooleate whereupon an emulsion having the consistency of a lotion containing, approximately, 64% by weight of the pentasiloxane was obtained as was suitable for use in cosmetic products.

EXAMPLE 3

Following the example of method 1, a water-emulsifier preblend consisting of 135 grams of polyoxyethylene 40 stearate and 100 grams sorbitan monostearate along with 300 grams of water was prepared. To this was added 1300 grams of decamethylpentasiloxane, which formed a grease-like emulsion. Formalin was added as an anti-bacterial agent.

EXAMPLE 4

An emulsifier preblend consisting of 255 grams of water, 82 grams polyoxyethylene 40 stearate and 67 grams sorbitan monostearate was prepared in accordance with the method in Example 1, whereupon this preblend was added to 900 grams of octamethyltetrasiloxane in order to form a paste-like emulsion.

EXAMPLE 5

An emulsion was formed from a 50—50 cyclic silicone mixture consisting of 450 grams octamethyltetrasiloxane and 450 grams decamethylpentasiloxane, which was formulated with an emulsifier-water preblend consisting of 82 grams polyoxyethylene 40 stearate and 57 grams sorbitan monostearate and 280 grams water. A silicone-water emulsion having a grease-like consistency was formed.

EXAMPLE 6

To 900 grams of decamethylpentasiloxane was added preblend consisting of 60 grams sorbitan monostearate and 200 grams of 70% octylphenoxypolyethoxy 39 ethanol and 200 grams water. Following the method described in Example 1 a silicone-water emulsion having soft paste-like consistency was formed.

EXAMPLE 7

An antiperspirant was formed by combining 100 grams of the silicone-water emulsion paste of Example 4 with 20 grams aluminum chlorhydrate in the form of Micr-Dry Ultrafine (Trademark of Releis Co.).

EXAMPLE 8

A skin freshener was formed by combining 100 grams of the silicone-water emulsion paste of Example 6 with 0.25% perfume.

EXAMPLE 9

A suntan lotion was formed by combining 100 grams of the silicone-water emulsion lotion of Example 2 with 3.0% homosalate and 0.25% perfume.

What is claimed as new and desired to be protected by Letters Patent of the United States is:

1. A silicone in water emulsion comprising:
   (A) 100 parts by weight of a cyclic polysiloxane or a combination of cyclic polysiloxanes of the formula:

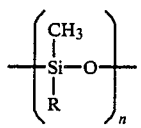

where n is an integer from 3 to 10, R is selected from the group consisting of $-CH_3$, $-(CH_2)_zCH_3$, $-CH_2CH_2CF_3$, $-CH=CH_2$, and $-C_6H_5$, and z is an integer from 1 to 10;
   (B) from 0.7 to 666 parts by weight of an emulsifier selected from the group consisting of ethoxylated fatty acids, ethoxylated and non-ethoxylated sorbitan esters, ethoxylated alkyl phenols, and ethoxylated ethers; and
   (C) from 5.0 to 960 parts by weight of water.

2. A composition as in claim 1, wherein said 100 parts of cyclic polysiloxane is added to 15 to 1000 parts of a preblended mixture of said water and emulsifier.

3. A composition as in claim 2 wherein the preblended water and emulsifier mixture is comprised of, (i) 100 parts by weight of one or more emulsifying agents and (ii) 50 to 2000 parts by weight water.

4. A silicone-water emulsion as in claim 1, further comprising an anti-bacterial agent.

5. A composition as in claim 1, wherein said silicone-water emulsion is a lotion.

6. A composition as in claim 1, wherein said silicone-water emulsion is a cream or paste.

7. A composition as in claim 1, wherein said silicone-water emulsion is an ointment or gel.

8. A silicone-water emulsion as in claim 1, further comprising from 0.1 to 20,000 parts by weight of one or more epidermal enhancing agents per 100 parts of said emulsion.

9. A composition as in claim 8, wherein said epidermal enhancing agent is a cosmetic or medicinal agent.

10. A composition as in claim 6, wherein said epidermal enhancing agent is a deodorant or antiperspirant.

11. An epidermal composition comprised of:
    (A) 0.1 to 20,000 parts by weight of one or more epidermal enhancing agents wherein said epidermal enhancing agents are contained in a vehicle comprised of:
    (B) 100 parts by weight of a silicone-water emulsion wherein said emulsion is comprised of (i) 100 parts by weight of a cyclic polysiloxane or a combination of cyclic polysiloxanes of the formula:

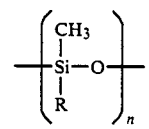

wherein n is an integer from 3 to 10, R is selected from the group consisting of $-CH_3$, $-(CH_2)_zCH_3$, $-CH_2CH_2CF_3$, $-CH=CH_2$, and $-C_6H_5$, and z is an integer from 1 to 10; and (ii) 0.7 to 666 parts by weight of an emulsifier and (iii) 5.0 to 960 parts water.

12. An epidermal enhancing composition as in claim 11, wherein said water and emulsifier is a preblended mixture comprised of (i) 100 parts by weight of one or more emulsifying agents selected from the group consisting of ethoxylated fatty acids, ethoxylated and non-ethoxylated sorbitan esters, ethoxylated alkyl phenols, and ethoxylated ethers, and (ii) 50 to 2000 parts water.

13. A composition as in claim 11, wherein said epidermal enhancing agent is a cosmetic.

14. A composition as in claim 11, wherein said epidermal enhancing agent is a medicine.

15. A composition as in claim 11, wherein said epidermal enhancing agent is an antiperspirant.

16. A composition as in claim 11, wherein said epidermal enhancing agent is a deodorant.

17. A composition as in claim 11, wherein said epidermal enhancing agent is applied in the form of a lotion.

18. A composition as in claim 11, wherien said epidermal enhancing agent is applied in the form of a paste.

19. A composition as in claim 11, wherein said epidermal enhancing agent is applied in the form of a cream.

20. A composition as in claim 11, wherein said epidermal enhancing agent is applied in the form of an ointment or gel.

21. The composition of claim 1 wherein the emulsifier is selected from the group consisting of
polyoxyethylene 8 stearate
polyoxyethylene 40 stearate
polyoxyethylene 50 stearate
sorbitan monolaurate
sorbitan monopalmitate
sorbitan monostearate
sorbitan tristearate
sorbitan monooleate
sorbitan trioleate
polyoxyethylene 20 sorbitan monolaurate
polyoxyethylene 4 sorbitan monolaurate
polyoxyethylene 20 sorbitan monopalmitate
polyoxyethylene 20 sorbitan monostearate
polyoxyethylene 20 sorbitan tristearate
polyoxyethylene 20 sorbitan monooleate
polyoxyethylene 5 sorbitan monooleate
polyoxyethylene 20 sorbitan trioleate
polyoxyethylene 4 lauryl ether
polyoxyethylene 23 lauryl ether
polyoxyethylene 20 cetyl ether
polyoxyethylene 10 stearyl ether
polyoxyethylene 20 oleyl ether
octylphenoxy polyethoxy ethanol
nonylphenoxy polyethoxy ethanol.

* * * * *